United States Patent
Prass et al.

[11] Patent Number: 5,665,844
[45] Date of Patent: Sep. 9, 1997

[54] POLYMER FILMS FOR DETECTING CHEMICAL SUBSTANCES

[75] Inventors: Werner Prass, Mainz; Thomas Stehlin, Hofheim, both of Germany; Yuan Liu, Kawagoe, Japan; Shizuo Ogura, Tsurugashima, Japan; Tetsu Yamamoto, Kawagoe, Japan; Akihiko Tokida, Kawagoe, Japan; Kenji Motosugi, Kawagoe, Japan

[73] Assignee: Hoechst Aktiengesellschaft, Frankfurt, Germany

[21] Appl. No.: 152,405

[22] Filed: Nov. 15, 1993

[30] Foreign Application Priority Data

Nov. 17, 1992 [JP] Japan .................... 4-307283

[51] Int. Cl.$^6$ .................................. C08F 220/10
[52] U.S. Cl. ............... 526/328; 526/328.5; 526/273; 526/329.2; 526/309; 526/330; 526/304; 526/329.5; 526/266; 526/320; 526/347.1; 526/334; 73/61.44
[58] Field of Search ............ 526/328, 328.5, 526/273, 329.5, 309, 330, 304, 266, 320, 347.1, 334; 73/61.44

[56] References Cited

U.S. PATENT DOCUMENTS

| | | |
|---|---|---|
| 5,015,843 | 5/1991 | Seitz et al. . |
| 5,194,540 | 3/1993 | Yamamoto et al. ............. 526/328 |
| 5,298,741 | 3/1994 | Walter et al. . |

FOREIGN PATENT DOCUMENTS

| | | |
|---|---|---|
| 3-096847 | 4/1991 | Japan . |
| WO81 00153 | 1/1981 | WIPO . |
| WO91 12626 | 8/1991 | WIPO . |

OTHER PUBLICATIONS

"Oxygen–Barrier Polymer Film for Packaging" Harrison et al EP518647–92–12–16 Abstract pp. 22–24 (In House Computer).

"Oxygen Barrier Polymer Film for Packaging" Harrison et al EP518646–92–12–16 Abstract pp. 24–27 (In House Computer).
English Abstract, JP–OS–No. 74485.
English Abstract, JP–OS–No. 96846.
English Abstract, JP–OS–No. 96847.
Brown et al., AIAA Paper No. 74–114, "Joint Conference on Sensing of Environmental Pollutants".
English Abstract, JP–OS–No. 238746.
English Abstract, JP–OS–No. 47531.

*Primary Examiner*—Joseph L. Schofer
*Assistant Examiner*—N. Sarofim
*Attorney, Agent, or Firm*—Curtis, Morris & Safford, P.C.

[57] ABSTRACT

The present invention pertains to a film for detecting chemical substances comprising a homopolymer or a copolymer having recurring units represented by the following formula (I):

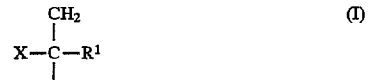

wherein X is —H, —F, —Cl, —Br, —CH$_3$, —CF$_3$, —CN or —CH$_2$CH$_3$; and R$^1$ is —R$^2$ or —Z—R$^2$;
wherein Z is —O—, —S—, —NH—, —NR$^{2'}$—, —(C=Y)—, —(C=Y)—Y—, —Y—(C=Y)—, —(SO$_2$)—, —Y'—(SO$_2$)—, —(SO$_2$)—Y'—, —Y'—(SO$_2$)—Y'—, —NH—(C=O)—, —(C=O)—NH—, —(C=O)—NR$^{2'}$—, —Y'—(C=Y)—Y'— or —O—(C=O)—(CH$_2$)$_n$—(C=O)—O—;
wherein Y is independently O or S, and Y' is independently O or NH, and n is an integer of 0 to 20;
and wherein R$^2$ and R$^{2'}$ represent independently a hydrogen atom, a linear alkyl group, a branched alkyl group, a cycloalkyl group, an unsaturated hydrocarbon group, an aryl group, a saturated or unsaturated hetero ring or derivatives thereof, provided that R$^1$ is not a hydrogen atom, a linear alkyl group or a branched alkyl group. The invention pertains also to a detector for chemical substances comprising such a film.

17 Claims, 2 Drawing Sheets

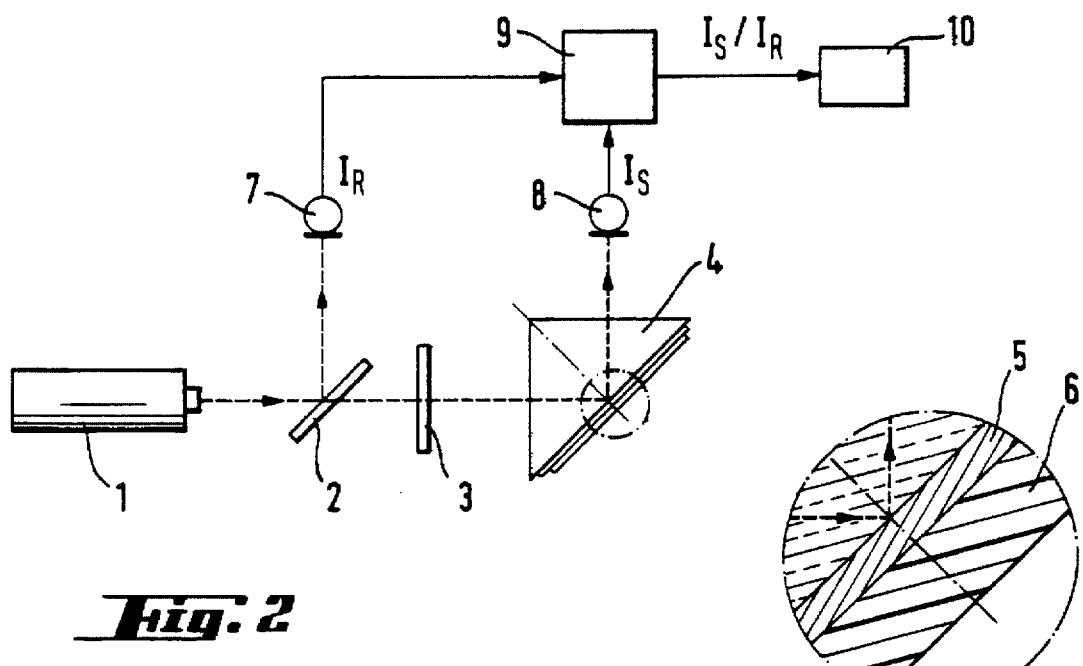
*Fig. 2*
*Fig. 2A*
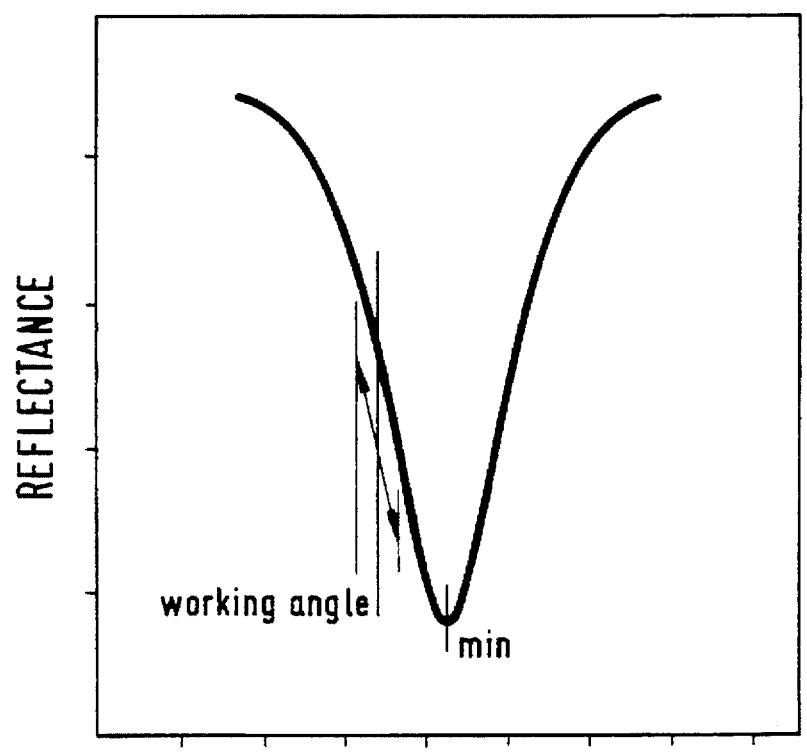
*Fig. 3*

POLYMER FILMS FOR DETECTING CHEMICAL SUBSTANCES

BACKGROUND OF THE INVENTION

This invention related to polymer films that are useful not only for detecting the presence of gaseous or liquid chemical substances but also for distinguishing one such chemical substance from another. In particular, the invention relates to polymer films that are capable of detecting gasoline vapor as distinguished from the vapor of diesel oil.

Providing automobiles with the wrong type of fuel is a common occurrence at gas stations. To prevent such accidents, the development of a new fuel detection system is strongly needed.

Conventional detectors of automotive fuels and other hydrocarbons are operated by either electrical or optical methods. An example of the electrical approach relies upon the adsorption of a substance to be detected on a semiconductor material, which causes a change in the resistance or conductance of the substance of interest. See, for example, Japanese Laid-Open Patent Application No. 74485/1975, which disclosed a gas detector that has two opposing electrodes provided on an insulating substrate, with a conductive powder containing a silicone rubber resistor being applied between the electrodes. Similar detectors are discloses in Japanese Laid-Open Patent Application Nos. 96846/1991 and 96847/1991, as well as German Laid-Open Patent Application No. 2,419,069 published Nov. 6, 1975. Brown et al. reported a method in which the change in the ion conductivity of a solid electrolyte (ion-exchange membrane) on account of gas adsorption is detected by polarography [See Proceedings of the Joint Conference on Sensing of Environmental Pollutants, AIAA Paper No. 71-1114, 1-3 (1971)]. A similar method is disclosed in British Patent Publication No. 2,185,579 A2. However, these methods have two problems in common: first, temperature control is indispensable for reliable detection and, secondly, the monitoring of temperature control requires complicated equipment.

Japanese Laid-Open Patent Application No. 285439/1988 discloses a sensor that detects the leakage of hydrocarbons on the basis of the change in the impedance of a coaxial cable.

These sensors which detect hydrocarbons electrically have an inherent problem in that they are prone to operate incorrectly in the presence of disturbances such as induction noise and that the hydrocarbons to be detected have the potential to explode if they catch fire due to a spark or some other phenomena.

An example of the optical approach is described in Japanese Laid-Open Patent Application No. 156838/1980, which discloses a method of detecting the presence of an oil or the like on the basis of a change in the refractive index of a porous material that occurs when it absorbs an oil or the like. A similar method that relief upon fiber optics using capillarity is disclosed in European Patent Publication No. 0,282,009 A2. Japanese Laid-Open Patent Application No. 238746/1985 discloses an apparatus that has an infrared detector on the inner surface of the side wall of a hydrocarbon gas conducting duct to detect the concentration of a hydrocarbon gas of interest on the basis of the change in the absorbance of infrared light. Laid-Open Japanese Patent Application No. 47531/1987 discloses a sensor that relies upon a shift from the propagation mode in an optical fiber to the leakage mode that occurs as a result of oil or water deposition on the inner surface of the fiber.

The conventional hydrocarbon detectors described above, whether they adopt the electrical or optical approach, are capable of detecting the presence of hydrocarbons but it is difficult for them to detect a plurality of hydrocarbons as distinguished from each other. In particular, it is extremely difficult to detect gasoline as distinguished from diesel oil which has very similar properties to gasoline. As a further problem, hydrocarbons have the danger of catching fire but none of the detectors available today are designed to assure utmost safety in this regard. In addition, these detectors are not only bulky but also expensive.

SUMMARY OF THE INVENTION

The present invention has been accomplished under these circumstances and has as an object to provide a detector that is capable of detecting a plurality of chemical substances as distinguished from each other in a safe manner.

Another object of the present invention is to provide a detector that is capable of detecting gasoline and diesel oil as distinguished from each other in a safe manner, The present inventors conducted intensive studies with a view to produce a film capable of detecting a plurality of chemical substances, particularly organic solvents and distinguishing them from each other. As a result, the present inventors found that specified side-chain groups in vinyl polymers had the ability to recognize molecules selectively and the present invention has been accomplished on the basis of this finding. According to the present invention, there is provided a film for detecting chemical substances that comprises a vinyl polymer having specified side-chain groups. The ability of such specified side-chain groups to recognize molecules can be utilized to distinguish cycloalkanes and benzenes from straight-chained alkanes. Similarly, hydrocarbons can be distinguished from alcohols, ketches, esters, ethers and halogenated hydrocarbons.

BRIEF DESCRIPTION OF THE DRAWINGS

FIG. 2 is a diagram showing the general layout of a chemical substance detector that is operated by the SPR method; FIG. 2A is an enlarged view of a portion of FIG. 2; and FIG. 3 is a graph showing the relationship between the angle of incidence and the intensity of reflected light as observed in the practice of the SPR method.

DESCRIPTION OF THE PREFERRED EMBODIMENTS

Figure 1:
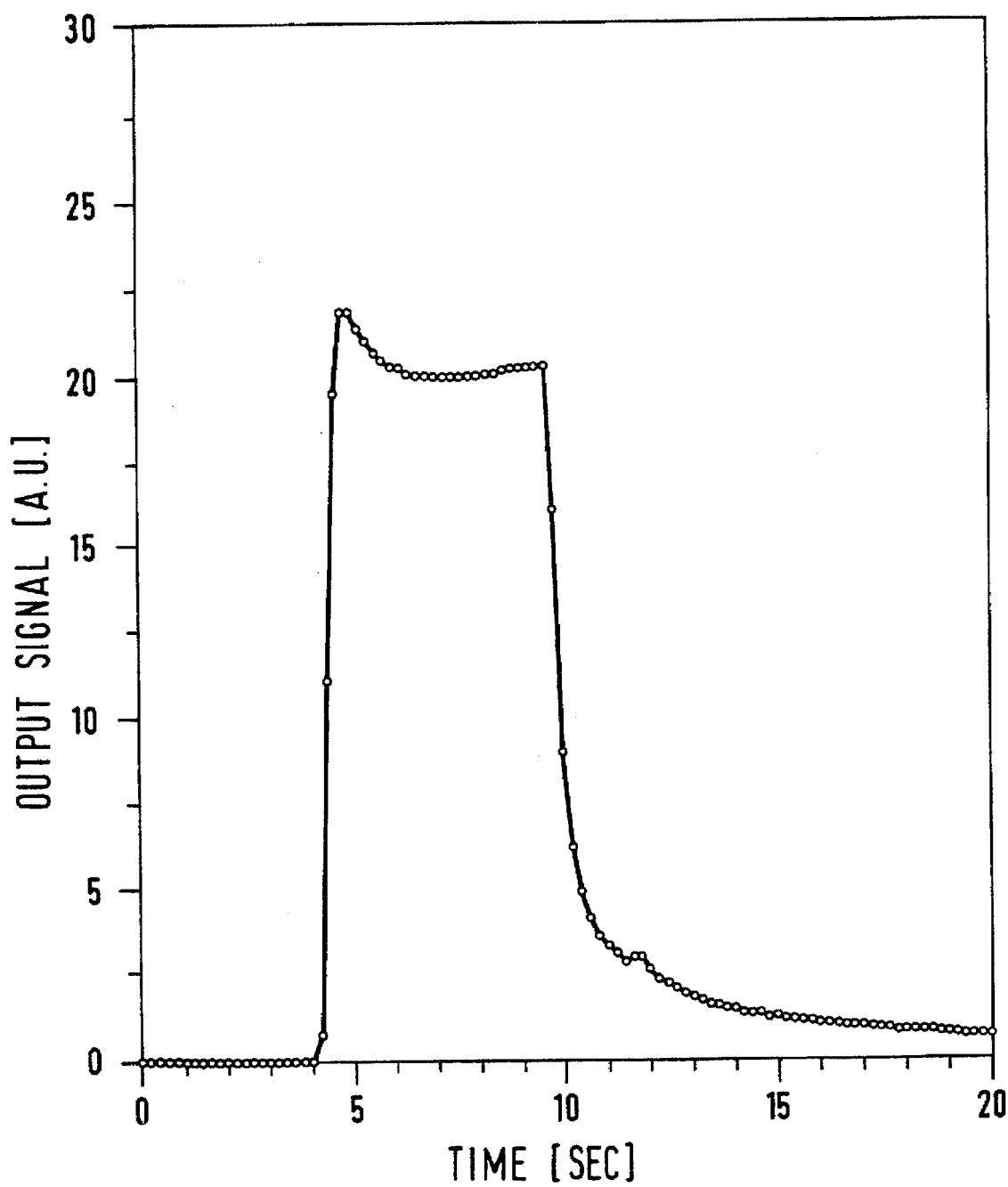
FIG. 1 is a graph showing the response to gasoline in case of detecting gasoline according to IER method using a thin layer of poly(2-ethylhexyl methacrylate-co-glycidyl methacrylate)

In accordance with the present invention, there is provided a film for detecting chemical substances that comprises a homopolymer or a copolymer that have a recurring unit represented by the following formula (I):

wherein

X is —H, —F, —Cl, —Br, —CH$_3$, —CF$_3$, —CN or —CH$_2$CH$_3$;

and R$_1$ is —R$^2$ or —Z—R$^2$ [where Z is —O—, —S—, —NH—, —NR$^{2'}$—, —(C=Y)—, —(C=Y)—Y—, —Y—(C=Y)—, (SO$_2$)—, —Y'—(SO$_2$)—, —(SO$_2$) —Y'—, —Y'—(SO$_2$)—Y'—, —NH—(C=O)—, —(C=O)—NH—, —(C=O)—NR$^2$'—, —Y'— (C=Y)—Y'— or —O—(C=O)—(CH$_2$)$_n$—(C=O)—O— (where Y is independently O or S, and Y' is independently O or NH, and n is an integer of 0 to 20), and R$^2$ and R$^2$' are independently a hydrogen atom, a linear alkyl group, a branched alkyl group, a cycloalkyl group, an unsaturated hydrocarbon group, an aryl group, a saturated or unsaturated hetero ring or derivatives thereof, provided that R$^1$ is not a hydrogen atom, a linear alkyl group or a branched alkyl group.

The interaction between chemical substances and side-chain groups in a vinyl polymer causes as the swelling of the polymer. Hence, the swelling of the polymer indicates the presence of a certain chemical substance and the degree of polymer swelling indicates the identity of that particular chemical substance. For example, aromatic hydrocarbons and cycloalkanes will interact more intensely with vinyl polymers having aromatic groups and branched alkyl or cycloalkyl groups in side chains than with vinyl polymers having linear alkyl groups in side chains; hence, the two types of polymers will swell by different degrees. As a result, it becomes possible for gasoline and diesel oil to be detected as distinguished from each other in the present invention. The applicability of the present invention was demonstrated within the temperature range of −40° to 80° C. which is generally held to be necessary for the purpose of detecting gasoline as distinguished from diesel oil. For finer distinction between chemical substances, it is advantageous to use a film that is formed from two or more polymers having different side chain groups or to use two or more films formed from different polymers.

The chemical substances detecting film of the present invention is comprised of a polymer having the recurring unit (I). Stated more specifically, the polymer may be a homopolymer comprising only the recurring unit (I) or it may be a copolymer comprising only the recurring unit (I) but also another recurring unit; alternatively, the polymer may be a copolymer comprising at least two kinds of the recurring unit (I); in the case where the chemical substance detecting film of the present invention is formed from a copolymer, the recurring units may be arranged in any way in the copolymer; for example, the chemical substance detecting film of the present invention may be formed from a random copolymer or an alternating copolymer or a block copolymer or a graft copolymer.

Preferable polymers to be used in the present invention have the recurring unit (I):

wherein X is N or CH$_3$; R$^1$ is a substituted or unsubstituted aryl group or —Z—R$^2$; z is —O—, —(C=O)—O— or —O—(C=O)—; and R$^2$ is a linear alkyl group, a branched alkyl group, a cycloalkyl group, an unsaturated hydrocarbon group, an aryl group, a saturated or unsaturated hetero ring or substituents thereof.

Polymers preferred for the purposes of the present invention include polymethacrylic acid esters and polyacrylic acid ester. The side-chain groups in these esters are preferably linear or branched alkyl groups or cycloalkyl groups, with the number of carbon atoms ranging preferably from 4 to 22.

Specific examples of the preferred polymers are listed below:
poly(dodecyl methacrylate);
poly(isodecyl methacrylate);
poly(2-ethylhexyl methacrylate);
poly(2-ethylhexyl methacrylate-co-methyl methacrylate);
poly(2-ethylhexyl metahcrylate-co-styrene);
poly(methyl methacrylate-co-2-ethylhexyl acrylate);
poly(methyl methacrylate-co-2-ethylhexyl methacrylate);
poly(isobutyl methacrylate-co-glycidyl methacrylate);
poly(cyclohexyl methacrylate);
poly(octadecyl methacrylate);
poly(octadecyl metahcrylate-co-styrene);
poly(vinyl propionate);
poly(dodecyl methacrylate-co-styrene);
poly(dodecyl methacrylate-co-glycidyl methacrylate);
poly(butyl methacrylate);
poly(butyl methacrylate-co-methyl methacrylate);
poly(butyl methacrylate-co-glycidyl methacrylate);
poly(2-ethylhexyl methacrylate-co-glycidyl methacrylate);
poly(cyclohexyl methacrylate-co-glycidyl methacrylate);
poly(cyclohexyl methacrylate-co-methyl methacrylate);
poly(benzyl methacrylate-co-2-ethylhexyl methacrylate);
poly(2-ethylhexyl methacrylate-co-diacetone acrylamide);
poly(2-ethylhexyl methacrylate-co-benzyl methacrylate-co-glycidyl methacrylate);
poly(2-ethylhexyl methacrylate-co-methyl methacrylate-co-glycidyl methacrylate);
poly(vinyl cinnamate);
poly(vinyl cinnamate-co-dodecyl methacrylate);
poly(tetrahydrofurfuryl methacrylate);
poly(hexadecyl methacrylate);
poly(2-ethylbutyl methacrylate);
poly(2-hydroxyethyl methacrylate);
poly(cyclohexyl methacrylate-co-isobutyl methacrylate);
poly(cyclohexyl methacrylate-co-2-ethylhexyl methacrylate);
poly(butyl methacrylate-co-2-ethylhexyl methacrylate);
poly(butyl methaerylate-co-isobutyl methacrylate);
poly(cyclohexyl methacrylate-co-butyl methacrylate);
poly(cyclohexyl methacrylate-co-dodecyl methacrylate);
poly(butyl methacrylate-co-ethyl methacrylate);
poly(butyl methacrylate-co-octadecyl methacrylate);
poly(butyl methacrylate-co-styrene);
poly(4-methylstyrene);
poly(cyclohexyl methacrylate-co-benzyl methacrylate);
poly(dodecyl methacrylate-co-benzyl methacrylate);
poly(octadecyl methacrylate-co-benzyl methacrylate);
poly(benzyl methacrylate-co-tetrahydrofurfuryl methacrylate);
poly(benzyl methacrylate-co-hexadecyl methacrylate);
poly(dodecyl methacrylate-co-methyl methacrylate);
poly(dodecyl methacrylate-co-ethyl methacrylate);
poly(2-ethylhexyl methacrylate-co-dodecyl methacrylate);
poly(2-ethylhexyl methacrylate-co-octadecyl methacrylate);
poly(2-ethylbutyl methacrylate-co-benzyl methacrylate);
poly(tetrahydrofurfuryl methacrylate-co-glycidyl methacrylate);
poly(4-methoxystyrene);
poly(2-ethylbutyl methacrylate-co-glycidyl methacrylate);
poly(styrene-co-tetrahydrofurfuryl methacrylate);
poly(2-ethylhexyl methacrylate-co-propyl methacrylate); and
poly(octadecyl methacrylate-co-isopropyl methacrylate).

Instead of the methacrylic acid ester polymers or copolymers listed above, those in which acrylic acid is substituted for methacrylic acid may preferably be used.

In the present invention, selectivity for certain kinds of chemical substances can be heightened by using a combination of specific monomers as a copolymer and adjusting its composition.

The polymers to form the chemical substance detecting film of the present invention may be crosslinkable on their own or they can be crosslinked by introducing compounds that have crosslinking reactive groups. Suitable crosslinking reactive groups include, for example, an amino group, a hydroxyl group, a carboxyl group, an epoxy group, a carbonyl group, a urethane group and derivatives thereof. Another example is a C=C double bond; exemplary compounds having this double bond include maleic acid, fumaric acid, sorbic acid, itaconic acid, cinnamic acid and derivatives thereof. Also useful as crosslinking agents are those substances which have such chemical structures as to be capable of forming carbenes or nitrenes upon exposure to visible light, ultraviolet rays or high-energy radiation. One of the advantages of crosslinking the polymers is that the films formed from crosslinked polymers are insoluble and hence exhibit enhanced stability. The methods of crosslinking the polymers are not limited in any particular way and various known crosslinking techniques, such as the thermal process and exposure to light or other radiation, can be employed.

Films can be formed from the polymers by any known film-forming techniques, such as spin coating, the casting of polymer solutions, and melt extrusion. For enhanced detection sensitivity, the film thickness is preferably kept as small as possible; hence, the preferred film-forming technique is one that is capable of forming films of reduced Thickness and it is particularly preferred to use the spin coating process.

If one wants to shorten the response time of chemical substance detection with the film of the present invention, it is desired to adjust the glass transition temperature of the film-forming polymer to be lower than the ambient temperature for detection.

In accordance with the second aspect of the present invention, there is provided a chemical substance detector that has the detecting film comprising the polymer described in previous paragraphs. As mentioned above, the chemical substance detecting film of the present invention swells upon interaction with chemical substances and this phenomenon can be used to detect chemical substances. In other words, physical changes (e.g., a change in weight, film thickness or refractive index) that accompany the swelling of the film can be used as a basis for detecting of chemical substances. Therefore, the chemical substance detector of the present invention comprises the chemical substance detecting film, as combined with a means for detecting the physical change that occurs in the detecting film. A preferred detection means is an optical one.

Exemplary optical detection means include interference enhanced reflection (IER), surface plasmon resonance (SPR), a Mach-Zehnder interferometer having different top coatings, and turning out of the propagation mode in optical waveguides on account of polymer swelling. In case of employing interference enhanced reflection as a detection means in the chemical substance detector of the present invention, it is particularly preferable since sensitivity is further increased.

Non-optical detection means can also be employed, as exemplified by electrical means and detection means that uses a crystal oscillator.

Interference enhanced reflection (IER) is a method that utilizes the reflection characteristic of a polymer film on a highly reflective substrate. Light reflected from the surface of a polymer film will interfere with light reflected at the interface between the polymer film and the substrate. The intensity of reflected light is largely dependent on the thickness and refractive index of the polymer film. Thus, the change in either the thickness of the polymer or its refractive index or the changes in both factors will appear as the change in the intensity of reflected light. Even in the case where a plurality of swollen polymer films behave differently, the degrees of swelling of the respective polymer films can be easily identified on the basis of the changes in the intensity of reflected light from the films. In short, the physical changes that occur in the chemical substance detecting film and which are used in IER are the changes in film thickness and refractive index.

Surface plasmon resonance (SPR) is a method in which light is incident on the metal-dielectric interface at the critical angle in such a way that the momentum and energy of photons at the interface will coincide with those of surface plasmons, whereby the metal-dielectric interface of interest can be excited optically. As a result, the energy of photons will couple with surface plasmons, causing a sharp drop in the intensity of reflected light. The efficiency of coupling with surface plasmons is greatly influenced not only by the thickness of the metal film but also by the characteristics of the dielectric on one side of the metal film. In short, the physical changes that occur in the chemical substance detecting film and which are used in SPR are also the changes in film thickness and refractive index.

The chemical substance detecting film of the present invention is preferably used together with a substrate that supports the film. Different substrates are to be used depending on the type of the means used to detect the physical changes that occur in the film. If IER is to be used as the detection means, a silicon wafer, glass, a polymer or a metal can be used as the substrate material. If SPR is to be used as the detection means, a thin metal film, preferably a thin silver or gold film, that have been formed on glass or transparent polymer may be used.

The following examples are provided for the purpose of further illustrating the present invention but are in no way to be taken as limiting.

EXAMPLE 1

Preparation of poly(2-ethylhexyl methacrylate)

2-Ethylhexyl methacrylate (19.83 g, 0.1 mol) and azobisisobutyronitrile (AIBN, 164 ml) were dissolved in tetrahydrofuran (100 ml) at 20° C. The resulting solution was purged with nitrogen for 1 hour. Then, the solution was refluxed by heating at 65° C. for 7 hours. During reflux, the solution was kept purged with nitrogen to prevent entrance of oxygen. The solution was cooled to 20° C. and subsequently poured into methanol (1 L), whereupon poly(2-ethylhexyl methacrylate) was precipitated. To further increase its purity, the poly(2-ethylhexyl methacrylate) was dissolved in tetrahydrofuran (50 ml) and subsequently allowed to precipitate in methanol (1 L). Finally, the viscous poly(2-ethylhexyl methacrylate) was collected and dried at 60 C under vacuum. Thereafter, the product poly(2-ethylhexyl methacrylate) was tested by thin-layer chromatography for detection of any residual monomer; as it turned out, the poly(2-ethylhexyl methacrylate) contained no residual monomer at all.

The final yield of the colorless clear poly(2-ethylhexyl methacrylate) was 12.2 g. This product was found to have a refractive index of 1.482 at 23° C. upon measurement with an Abbe refractometer.

An elemental analysis of the product gave the results shown below. Calculation was made on the assumption that poly(2-ethylhexyl methacrylate) is expressed by $C_{12}H_{22}O_2$ with a molecular weight of 198.31.

|  | Carbon (%) | Hydrogen (%) |
| --- | --- | --- |
| Calculated | 72.68 | 11.18 |
| Found | 72.4 | 11.2 |

The product was also subjected to gel permeation chromatography. Tetrahydrofuran was used as a solvent and polystyrene was used as a standard for calibration. As it turned out, the poly(2-ethylhexyl methacrylate) had a weight average molecular weight (MW) of 63,100 and a number average molecular weight (Mn) of 30,400, with the molecular weight distribution (Mw/Mn) being 2.08.

EXAMPLE 2

Preparation of poly(2-ethylhexyl methacrylate-co-methyl methacrylate)

2-Ethylhexyl acrylate (18.428 g, 0.1 mol), methyl methacrylate (20.024 g, 0.2 mol) and AIBN (164 mg) were dissolved in tetrahydrofuran (100 ml) at 20° C. The resulting solution was purged with nitrogen for 1 hour. Then, the solution was refluxed by heating at 65° C. for 7 hours. During reflux, the solution was purged with nitrogen to prevent the entrance of oxygen. The solution was cooled to 20° C. and subsequently poured into methanol (800 ml), whereupon poly(2-ethylhexyl methacrylate-co-methyl methacrylate) was precipitated. To further increase its purity, the poly(2-ethylhexyl methacrylate-co-methyl methacrylate) was dissolved in tetrahydrofuran (100 ml) and subsequently allowed to precipitate in methanol (800 ml). Finally, the produce poly(2-ethylhexyl methacrylate-co-methyl methacrylate) was collected and dried at 60° C. under vacuum. Thereafter, the produce poly(2-ethylhexyl methacrylate-co-methyl methacrylate) was tested by thin-layer chromatography for detection of any residual monomer; as it turned out, the poly(2-ethylhexyl methacrylate-co-methyl methacrylate) contained no residual monomer at all.

The final yield of the colorless clear poly(2-ethylhexyl methacrylate-co-methyl methacrylate) was 15.3 g. This product was found to have a refractive index of 1.457 at 24° C. upon measurement with an Abbe refractometer.

The product was also found to have a glass transition temperature of 22° C. upon measurement with a differential scanning calorimeter (DSC7 of Perkin Elmer). The rate of temperature elevation in DSC was 10° C./min.

An elemental analysis of the product showed that it had a carbon content of 64.65% and a hydrogen content of 9.41%. These data show that the mole fractions of the two comonomers in the product were 0.29 for 2-ethylhexyl methacrylate and 0.71 for methyl methacrylate.

The product was also subjected to gel permeation chromatography, with tetrahydrofuran being used as a solvent and polystyrene as a standard for calibration. As it turned out, the poly(2-ethylhexyl methacrylate-co-methyl methacrylate) had a weight average molecular weight (Mw) of 57,800 and a number average molecular weight (Mn) of 32,500, with the molecular weight distribution (Mw/Mn) being 1.8.

EXAMPLE 3

Preparation of poly(dodecyl methacrylate)

Dodecyl methacrylate (50.882 g, 0.2 mol) and AIBN (164 mg) were dissolved in tetrahydrofuran 100 ml) at 20° C. The resulting solution was purged with nitrogen for 1 hour. Then, the solution was refluxed by heating at 65° C. for 7 hours. During reflux, the solution was purged with nitrogen to prevent the entrance of oxygen. The solution was cooled to 20° C. and subsequently poured into methanol (800 ml), whereupon poly(dodecyl methacrylate) was precipitated. To further increase its purity, the poly(dodecyl methacrylate) was dissolved in tetrahydrofuran (100 ml) and subsequently allowed to precipitate in methanol (800 ml). Finally, the viscous poly(dodecyl methacrylate) was collected and dried at 60° C. under vacuum. Thereafter, the product poly(dodecyl methacrylate) was tested by thin-layer chromatography for detection of any residual monomer; as it turned out, the poly(dodecyl methacrylate) contained no residual monomer at all.

The final yield of the colorless clear poly(dodecyl methacrylate) was 23.6 g. This product was found to have a refractive index of 1.474 at 24° C. upon measurement with an Abbe refractometer.

An elemental analysis of the product gave the results shown below. Calculation was made on the assumption that poly(dodecyl methacrylate) is expressed by $C_{16}N_{30}O_2$ with a molecular weight of 254.41.

|  | Carbon (%) | Hydrogen (%) |
| --- | --- | --- |
| Calculated | 75.54 | 11.89 |
| Found | 75.5 | 12.0 |

The product was also subjected to gel permeation chromatography. Tetrahydrofuran was used as a solvent and polystyrene was used as a standard for calibration. As it turned out, the poly(dodecyl methacrylate) had a weight average molecular weight (Mw) of 111,100 and a number average molecular weight (Mn) of 49,000, with the molecular weight distribution (Mw/Mn) being 2.3.

EXAMPLE 4

Preparation of poly(2-ethylhexyl methacrylate-co-styrene)

2-ethylhexyl methacrylate (19.83 g, 0.1 mol), styrene (10.4 g, 0.1 mol) and AIBN (0.164 mg) were dissolved in tetrahydrofuran (120 ml) at 20° C. The resulting solution was purged with nitrogen for 1 hour. Then, the solution was refluxed by heating at 65° C. for 7 hours. During reflux, the solution was purged with nitrogen to prevent the entrance of oxygen. The solution was cooled to 20° C. and subsequently poured into hexane (800 ml); whereupon poly(2-ethylhexyl methacrylate-co-styrene) was precipitated. To further increase its purity, the poly(2-ethylhexyl methacrylate-co-styrene) was dissolved in tetrahydrofuran (50 ml) and subsequently allowed to precipitate in hexane (800 ml). Finally, the product poly(2-ethylhexyl methacrylate-co-styrene) was collected and dried at 60° C. under vacuum. Thereafter, the product poly(2-ethylhexyl methacrylate-co-styrene) was tested by thin-layer chromatography for detection of any residual monomer; as it turned out, the poly(2-ethylhexyl methacrylate-co-styrene) contained no residual monomer at all.

The final yield of the colorless clear poly(2-ethylhexyl methacrylate-co-styrene) was 19.8 g. This product was found to have a refractive index of 1.522 at 23° C. upon measurement with an Abbe refractometer.

The product was also found to have a glass transition temperature of 13° C. upon measurement with a differential scanning calorimeter (DSC7 of Perkin Elmer). The rate of temperature elevation in DSC was 10° C./min.

An elemental analysis of the product showed that it had a carbon content of 79.58% and a hydrogen content of 9.96%. These data show that the mole fractions of the two comonomers in the product were 0.49 for 2-ethylhexyl methacrylate and 0.51 for styrene.

The product was also subjected to gel permeation chromatography. Tetrahydrofuran was used as a solvent and polystyrene was used as a standard for calibration. As it turned out, the poly(2-ethylhexyl methacrylate-co-styrene) had a weight average molecular weight (Mw) of 50,300 and a number average molecular weight (Mn) of 29,300, with the molecular weight distribution (Mw/Mn) being 1.73.

EXAMPLE 5

Preparation of poly(isobutyl methacrylate-co-glycidyl methacrylate)

Isobutyl methacrylate (30.0 g, 0.21 mol), glycidyl methacrylate (1.58 g, 0.00222 mol) and AIBN (164 mg) were dissolved in tetrahydrofuran (300 ml) at 20° C. The resulting solution was purged with nitrogen for 1 hour. Then, the solution was refluxed by heating at 65° C. for 7 hours. During reflux, the solution was purged with nitrogen to prevent the entrance of oxygen. The solution was cooled to 20° C. and subsequently poured into hexane (800 ml), whereupon poly(isobutyl methacrylate-co-glycidyl methacrylate) was precipitated. To further increase its purity, the poly(isobutyl methacrylate-co-glycidyl methacrylate) was dissolved in tetrahydrofuran (50 ml) and subsequently allowed to precipitate In methanol (800 ml). Finally, the product poly(isobutyl methacrylate-co-glycidyl methacrylate) was collected and dried at 60° C. under vacuum. Thereafter, the product poly(isobutyl methacrylate-co-glycidyl methacrylate) was tested by thin-layer chromatography for detection of any residual monomer; as it turned out, the poly(isobutyl methacrylate-co-glycidyl methacrylate) contained no residual monomer at all.

The final yield of the colorless clear poly(isobutyl methacrylate-co-glycidyl methacrylate) was 16 g. This product was found to have a refractive index of 1.475 at 22° C. upon measurement with an Abbe refractometer.

The product was also found to have a glass transition temperature of 29.0° C. upon measurement with a differential scanning calorimeter (DSC7 of Perkin Elmer). The rate of temperature elevation was 10° C./min.

An elemental analysis of the product showed that it had a carbon content of 86.9% and a hydrogen content of 9.92%. These data show that the mole fractions of the two comonomers in the product were 0.93 for isobutyl methacrylate and 0.07 for glycidyl methacrylate.

The product was also subjected to gel permeation chromatography. Tetrahydrofuran was used as a solvent and polystyrene was used as a standard for calibration. As it turned out, the poly(isobutyl methacrylate-co-glycidyl methacrylate) had a weight average molecular weight (Mw) of 61,000 and a number average molecular weight (Mn) of 40,500, with the molecular weight distribution (Mw/Mn) being 1.55.

EXAMPLE 6

Detecting the Vapors of Hydrocarbons by Interference Enhanced Reflection

The vapours of gasoline, diesel oil and other hydrocarbons were detected optically at room temperature by interference enhanced reflection (IER) using chemical substance detecting polymer films prepared in accordance with the present invention.

The polymers used to implement the IER technique are listed in Table 1. These polymers were dissolved in cyclohexanone to make solutions having concentrations in the range 5–10 wt %; the solutions were then spin coated on silicon substrates. The coated films were baked for ca. 1.5 hours under vacuum around the glass transition temperature of the polymers. The films thus prepared were measured for thickness with a surface texture analyzing system 3030 ST of DEKTAK Corp. To attain a maximum detection sensitivity, the thickness of polymer films should be less than 1 μm; in Example 1, the polymer films were typically about 130 nm in thickness.

During measurement by the IER technique, each of the polymer films on silicon substrate was placed in a closed flow-through cell that was adapted to be supplied with the vapors of gasoline, diesel oil and other chemical substances together with air or nitrogen. The vapors of gasoline and other hydrocarbons to be detected were prepared by bubbling air or nitrogen through the hydrocarbons in a liquid state. Besides gasoline and diesel oil, two chemical substances were used: hexane and toluene.

Light from a He-Ne laser was applied onto each polymer film at an incident angle of 70°. The laser light had been polarized linearly in a direction normal to the plane of incidence. The intensity of reflected light was monitored with a photodetector, the output of which was recorded on a chart recorder and a personal computer (Compaq 386 PC).

The results of measurements are shown in Table 1 in terms of "sensitivity", which is expressed as the percentage of the relative change in the intensity of reflected light.

As is clear from Table 1, the sensitivity of measurement varied with the kind of hydrocarbons to be detected. It should be particularly noted that the difference in sensitivity between gasoline and diesel oil was very significant.

TABLE 1

| Polymer | Hexane | Toluene | Gasoline | Diesel oil |
|---|---|---|---|---|
| PMMA | 0.0 | 0.0 | 0.0 | 0.0 |
| PiDMA | 28.5 | 25.2 | 31.8 | 3.3 |
| CoP(EHMA-St) | 26.0 | 55.0 | 39.0 | 1.5 |
| PEHMA | 14.6 | 38.5 | 24.6 | 2.1 |
| CoP (MMA-EHA) | 6.5 | 24.4 | 24.5 | 0.0 |
| CoP (MMA-EHMA) | 0.0 | 13.8 | 5.1 | 0.0 |
| PCHA | 2.1 | 6.1 | 7.3 | 2.1 |
| PDDMA | 124.3 | 115.9 | 84.3 | 8.6 |
| PVP | 14.0 | 46.8 | 23.8 | 1.8 |

Key to symbols
PMMA: poly(methyl methacrylate)
PiDMA: poly(isodecyl methacrylate)
CoP(EHMA-St): poly(2-ethylhexyl methacrylate-co-styrine)(EHMA:St = 0.49:0.51)
PEHMA: poly(ethylhexyl methacrylate)
CoP(MMA-EHA): poly(methyl methacrylate-co-2-ethylhexyl acrylate) (MMA:EHA = 0.71:0.29)
CoP(MMA-EHMA): poly(methyl methacrylate-co-2-ethylhexyl methacrylate) (MMA:EHMA = 0.62:0.38)
PCHA: poly(cyclohexyl acrylate)
PDDMA: poly(dodecyl methacrylate)
PVP: poly(vinyl propionate)

Comparative Example

The detection of the vapors of hydrocarbons was carried out in the same procedure as in Example 6 except that thin films of poly(ethylene adipate), poly(ethylene terephthalate), poly(1,4-butylene terephthalate), poly (ethylene succinate), poly(ε-caprolactam), nylon 66, cellulose and polyacrylonitrile were used instead of the thin film used in Example 6, but sufficient sensitivity could not be obtained.

EXAMPLE 7

Preparation of poly(tetrahydrofurfuryl methacrylate)

Tetrahydrofurfuryl methacrylate (17.021 g, 0.1 mol) and AIBN (164 mg) were dissolved in tetrahydrofuran (100 ml) at 20° C. The resulting solution was purged with nitrogen for 1 hour. Then, the solution was refluxed by heating at 65° C. for 4 hours. During the reflux, the solution was purged with nitrogen to prevent the entrance of oxygen. The solution was cooled to 20° C. and subsequently poured into methanol (800 ml), whereupon poly(tetrahydrofurfuryl methacrylate) was precipitated. To further increase its purity, the poly(tetrahydrofurfuryl methacrylate) was dissolved in tetrahydrofuran (100 ml) and subsequently allowed to precipitated in methanol (1.0 l). Finally, the product poly (tetrahydrofurfuryl methacrylate) was collected and dried at 60° C. under vacuum. Thereafter, the product poly (tetrahydrofurfuryl methacrylate) was tested by thin-layer chromatography for detection of any residual monomer; as it turned out, the poly(tetrahydrofurfuryl methacrylate) contained no residual monomer at all.

The final yield of the colorless clear poly (tetrahydrofurfuryl methacrylate) was 12.53 g. A 5 weight % THF solution of the poly(tetrahydrofurfuryl methacrylate) was prepared and spin-coated onto a silicone base to prepare a thin film; the product was found to have a refractive index of 1.503 at 23° C. upon measurement with a three-wavelength automatic ellipsometer Auto EL IV NIR III of Rudolf Research.

The poly(tetrahydrofurfuryl methacrylate) was also found to have a glass transition temperature of 49° C. upon measurement with a differential scanning calorimeter (DSC7 of Perkin Elmer). The rate of temperature elevation in DSC was 20° C./min.

The poly(tetrahydrofurfuryl methacrylate) was also subjected to gel permeation chromatography. Tetrahydrofuran was used as a solvent and polystyrene was used as a standard for calibration. As it turned out, the poly(tetrahydrofurfuryl methacrylate) had a weight average molecular weight (Mw) of 95,800 and a number average molecular weight (Mn) of 45,200, and the molecular weight distribution (Mw/Mn) was 2.12.

EXAMPLE 8

Preparation of poly(2-ethylhexyl methacrylate-co-glycidyl methacrylate)

2-ethylhexyl methacrylate (19.83 g, 0.1 mol), glycidyl methacrylate (14.22 g, 0.1 mol) and AIBN (164 mg) were dissolved in tetrahydrofuran (120 ml) at 20° C. The resulting solution was purged with nitrogen for 1 hour. Then, the solution was refluxed by heating at 65° C. for 7 hours. During the reflux, the solution was purged with nitrogen to prevent the entrance of oxygen. The solution was cooled to 20° C. and subsequently poured into methanol (1.2 l), whereupon poly(2-ethylhexyl methacrylate-co-glycidyl methacrylate) was precipitated. To further increase its purity, the poly(2-ethylhexyl methacrylate-co-glycidyl methacrylate) was dissolved in tetrahydrofuran (100 ml) and subsequently allowed to precipitate in methanol (1.5 l). Finally, the product poly(2-ethylhexyl methacrylate-co-glycidyl methacrylate) was collected and dried at 60° C. under vacuum. Thereafter, the product poly(2-ethylhexyl methacrylate-co-glycidyl methacrylate) was tested by thin-layer chromatography for detection of any residual monomer; as it turned out, the poly(2-ethylhexyl methacrylate-co-glycidyl methacrylate) contained no residual monomer at all.

The final yield of the colorless clear poly(2-ethylhexyl methacrylate-co-glycidyl methacrylate) was 29.7 g. A 10 weight % cyclohexanone solution of the poly(2-ethylhexyl methacrylate-co-glycidyl methacrylate) was prepared and spin-coated onto a silicone substrate to prepare a thin film; the product was found to have a refractive index of 1.498 at 23° C. upon measurement with a Three-wavelength automatic ellipsometer Auto EL IV NIR III of Rudolf Research.

The poly(2-ethylhexyl methacrylate-co-glycidyl methacrylate) was also found to have a glass transition temperature of 29° C. upon measurement with a differential scanning calorimeter (DSC7 of Perkin Elmer). The rate of temperature elevation in DSC was 10° C./min.

An elemental analysis of the poly(2-ethylhexyl methacrylate-co-glycidyl methacrylate) showed that it had a carbon content of 66.53% and a hydrogen content of 9.54%. These data show that the mole fractions of the two comonomers in the poly(2-ethylhexyl methacrylate-co-glycidyl methacrylate) were 0.5 for 2-ethylhexyl methacrylate and 0.5 for glycidyl methacrylate.

The poly(2-ethylhexyl methacrylate-co-glycidyl methacrylate) was also subjected to gel permeation chromatography. Tetrahydrofuran was used as a solvent and polystyrene was used as a standard for calibration. As it turned out, the poly(2-ethylhexyl methacrylate-co-glycidyl methacrylate) had a weight average molecular weight (Mw) of 95,000 and a number average molecular weight (Mn) of 42,000, and the molecular weight distribution (Mw/Mn) was 2.26.

EXAMPLE 9

Preparation of poly(benzyl methacrylate-co-2-ethylhexyl methacrylate)

Benzyl methacrylate (24.67 g, 0.14 mol), 2-ethylhexyl methacrylate (13.88 g, 0.07 mol) and AIBN (164 mg) were dissolved in tetrahydrofuran (100 ml) at 20° C. The resulting solution was purged with nitrogen for 1 hour. Then, the solution was refluxed by heating at 65° C. for 6 hours. During the reflux, the solution was purged with nitrogen to prevent the entrance of oxygen. The solution was cooled to 20° C. and subsequently poured into methanol (1 l), whereupon poly(benzyl methacrylate-co-2-ethylhexyl methacrylate) was precipitated. To further increase its purity, the poly(benzyl methacrylate-co-2-ethylhexyl methacrylate) was dissolved in tetrahydrofuran (50 ml) and subsequently allowed to precipitate in methanol (1 l). Finally, the product poly(benzyl methacrylate-co-2-ethylhexyl methacrylate) was collected and dried at 60° C. under vacuum. Thereafter, the product poly(benzyl methacrylate-co-2-ethylhexyl methacrylate) was tested by thin-layer chromatography for detection of any residual monomer; as it turned out, the poly(benzyl methacrylate-co-2-ethylhexyl methacrylate) contained no residual monomer at all.

The final yield of the colorless clear poly(benzyl methacrylate-co-2-ethylhexyl methacrylate) was 34.5 g. A 10 weight % cyclohexanone solution of the poly(benzyl methacrylate-co-2-ethylhexyl methacrylate) was prepared and spin-coated onto a silicone substrate to prepare a thin film; the product was found to have a refractive index of 1.534 at 23° C. upon measurement with a three-wavelength automatic ellipsometer Auto, EL IV NIR III of Rudolf Research.

The poly(benzyl methacrylate-co-2-ethylhexyl methacrylate) was also found to have a glass transition temperature of 36.0° C. upon measurement with a differential scanning calorimeter (DSC7 of Perkin Elmer). The rate of temperature elevation in DSC was 10° C./min.

An elemental analysis of the poly(benzyl methacrylate-co-2-ethylhexyl methacrylate) showed that it had a carbon content of 74.56% and a hydrogen content of 8.62%. These data show that the mole fractions of the two comonomers in the poly(benzyl methacrylate-co-2-ethylhexyl methacrylate) were 0.73 for benzyl methacrylate and 0.27 for 2-ethylhexyl methacrylate.

The poly(benzyl methacrylate-co-2-ethylhexyl methacrylate) was also subjected to gel permeation chromatography. Tetrahydrofuran was used as a solvent and polystyrene was used as a standard for calibration. As it turned out, the poly(benzyl methacrylate-co-2-ethylhexyl methacrylate) had a weight average molecular weight (Mw) of 88,800 and a number average molecular weight (Mn) of 37,100, and the molecular weight distribution (Mw/Mn) was 2.42.

EXAMPLE 10

Preparation of poly(butyl methacrylate)

Butyl methacrylate (14.22 g, 0.1 mol) and AIBN (164 mg) were dissolved in tetrahydrofuran (100 ml) at 20° C. The resulting solution was purged with nitrogen for 1 hour. Then, the solution was refluxed by heating at 65° C. for 7 hours. During the reflux, the solution was purged with nitrogen to prevent the entrance of oxygen. The solution was cooled to 20° C. and subsequently poured into methanol (1 l), whereupon poly(butyl methacrylate) was precipitated. To further increase its purity, the poly(butyl methacrylate) was dissolved in methylene chloride (50 ml) and subsequently allowed to precipitate in methanol (800 ml). Finally, viscous poly(butyl methacrylate) was collected and dried at 60° C. under vacuum. Thereafter, the product poly(butyl methacrylate) was tested by thin-layer chromatography for detection of any residual monomer; as it turned out, the poly(butyl methacrylate) contained no residual monomer at all.

The final yield of the colorless clear poly(butyl methacrylate) was 8.44 g. A 5 weight % cyclohexanone solution of the poly(butyl methacrylate) was prepared and spin-coated onto a silicone substrate to prepare a thin film; the product was found to have a refractive index of 1.480 at 23° C. upon measurement with a three-wavelength automatic ellipsometer Auto EL IV NIR III of Rudolf Research.

An elemental analysis of the poly(butyl methacrylate) gave the results shown below. Calculation was made on the assumption that poly(butyl methacrylate) is expressed by $C_8H_{14}O_2$ with a molecular weight of 142.2.

|  | Carbon (%) | Hydrogen (%) |
| --- | --- | --- |
| Calculated | 67.57 | 9.92 |
| Found | 67.75 | 10.01 |

The poly(butyl methacrylate) was also subjected to gel permeation chromatography. Tetrahydrofuran was used as a solvent and polystyrene was used as a standard for calibration. As it turned out, the poly(butyl methacrylate) had a weight average molecular weight (Mw) of 45,000 and a number average molecular weight (Mn) of 22,500, and the molecular weight distribution (Mw/Mn) was 2.0.

EXAMPLE 11

Preparation of poly(2-ethylhexyl methacrylate-co-glycidyl methacrylate)

Poly(2-ethylhexyl methacrylate-co-glycidyl methacrylate) (1.0 g) and 4,4-diaminodiphenylmethane (0.201 g, 1.015 mmol) were dissolved in cyclohexanone to make a total amount of 20 g. The solution was dropped on a silicone substrate and spin-coated by rotating at 4000 rpm for 30 seconds. After the film was dried at 60° C. under vacuum for 2 hours, it was heated at 150° C. for 2 hours to crosslink polymers. Thus, an insoluble thin film of poly(2-ethylhexyl methacrylate-co-glycidyl methacrylate) with a thickness of 165.0 nm was obtained.

EXAMPLE 12

Detecting the Vapors of Chemical Substances by Interference Enhanced Reflection

The vapors of gasoline, diesel oil and other organic solvents were detected optically at room temperature in the same manner as in Example 6 by interference enhanced reflection (IER) using chemical substance detecting polymer films in accordance with the present invention. The polymers used are listed in Table 2. The organic chemical substances used in the present Example were gasoline, diesel oil, acetone, dichloromethane, diethyl ether, ethanol, hexane and toluene. Response to gasoline in case of using a thin film of poly(2-ethylhexyl methacrylate-co-glycidyl methacrylate) was recorded every 0.2 seconds and shown in FIG. 1.

TABLE 2

| Organic Solvent | CoP (BZMA-EHMA) | CoP (EHMA-GLMA) | PBMA | PTHFMA |
| --- | --- | --- | --- | --- |
| Acetone | 144.4 | 26.9 | 59.1 | 143.7 |
| Dichloromethane | 233.3 | 37.1 | 31.8 | 319.5 |
| Diesel | 1.5 | 2.0 | 2.3 | 2.3 |
| Diethyl ether | 159.3 | 2.0 | 77.3 | 65.5 |
| Ethanol | 37.8 | 13.2 | 10.5 | 63.2 |
| Ethyl Acetate | 177.8 | 26.9 | 40.9 | 101.1 |
| Gasoline | 129.6 | 21.8 | 62.3 | 26.5 |
| Hexane | 57.8 | 9.1 | 29.5 | 5.7 |
| Toluene | 196.3 | 30.5 | 86.4 | 66.7 |

Key to symbols
CoP(BZMA-EHMA): poly(benzyl methacrylate-co-2-ethylhexyl methacryate) (BZMA:EHMA = 0.73:0.27)
CoP(EHMA-GLMA): poly(2-ethylhexyl methacrylate-co-glycidyl methacryate) (EHMA:GLMA = 0.5:0.5)
PBMA: poly(butyl methacryate)
PTHFMA: poly(tetrahydrofurfuryl methacryate)

As is clear from FIG. 1, gasoline could be detected in such a short time as 1 second.

In addition, as is clear from the results in Table 2, the sensitivity of measurement varied with the kind of chemical substances. Hence, it is possible to measure various chemical substances simultaneously by combining a plurality of films.

EXAMPLE 13

Detecting the Vapors of Hydrocarbons by Surface Plasmon Resonance

To achieve optimal coupling between incident light ($\lambda=632.8$ nm) and surface plasmons, a thin silver film was formed in a thickness of 50 nm on a slide glass substrate by vacuum evaporation. Poly(2-ethylhexyl methacrylate-co-styrene) as dissolved in cyclohexane at a concentration of 2.5 wt % was spin coated on the surface of the thin silver film. The polymer film thus prepared had a thickness of ca. 50 nm. After the completion of spin coating, the polymer film was placed under vacuum and dried at around the glass transition temperature of the polymer.

The general layout of the SPR equipment used in Example 2 is shown in FIG. 2. Light from a He-Ne laser 1 was divided into two beams by a beam splitter 2. One of the split beams was P-polarized with a polarizer 3. The polarized beam passed through a flint glass right-angle prism 4 (n=1.745), and the glass slide, and was then incident upon the thin silver film 5. The prism 4 was placed in contact with the slide glass (n=1.5143). For index matching between the prism 4 and the slide glass, the gap between the two members was filled with an immersion oil (n=1.514). The assembly consisting of the prism and the glass slide coated with the thin silver film and polymer films was placed in a flow-through cell (not shown) in such a way that the polymer film 6 would face inward of the cell. The critical angle for the excitation of surface plasmons was determined by varying the incident angle of laser light. When the vapors of gasoline and other hydrocarbons were admitted into the cell, the interaction of the polymer film 6 with the vapor to be detected was monitored by recording the reflectance of light at a fixed incident angle corresponding to half the maximum reflectivity on one side of the resonance (see FIG. 3). The intensity of reflected light was measured with a photodetector 8 at room temperature. The photodetector 8 generates an electric signal $I_S$ in proportion to the intensity of the reflected light it receives. Another photodetector 7 measures the reference beam (the other of the two beams emerging from the beam splitter 2) and converts it to an electric signal $I_R$. The two electronic signals $I_S$ and $I_R$ are fed into to electronic circuitry 9, which outputs $I_S/I_R$ as a measurement signal. The output signal is recorded by an appropriate recording means 10.

The hydrocarbons to be detected other than gasoline were toluene, hexane and diesel oil. The equipment shown in FIG. 1 was capable of measuring with high sensitivity the change in the thickness and refractive index of polymer film 6 due to its interaction with hydrocarbon vapors. The results are shown in Table 3 in terms of "sensitivity", which is expressed as the percentage of the relative change in the intensity of reflected light ($\delta R/R$).

As is clear from Table 3, the sensitivity of measurement varied with the kind of hydrocarbons to be detected. It should be particularly noted that the sensitivity to gasoline was higher than that to diesel oil by one order of magnitude.

TABLE 3

| Hydrocarbon | $\delta R/R$ (%) |
|---|---|
| toluene | 320.74 |
| hexane | 239.74 |
| gasoline | 134.84 |
| diesel oil | 12.83 |

What is claimed is:

1. A film for detecting chemical substances comprising a homopolymer or a copolymer having recurring unite represented by the following formula (I):

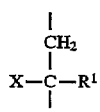
(I)

wherein X is —H, —F, —Cl, —Br, —CH$_3$, —CF$_3$, —CN or —CH$_2$C$_3$; and R$^1$ is —R$^2$ or —Z—R$^2$;

wherein Z is —O—, —S—, —NH—, —NR$^{2'}$—, —(C=Y)—, —(C=Y)—Y—, —Y—(C=Y)—, —(SO$_2$)—, —Y'—(SO$_2$)—, —(SO$_2$)—Y'—, —Y'—(SO$_2$)—Y'—, —NH—(C=O)—, —(C=O)—NH—, —(C=O)—NR$^{2'}$—, —Y'—(C=Y)—Y'— or —O—(C=O)—(CH$_2$)$_n$—(C=O)—O—;

wherein Y if independently O or S, and Y' is independently O or NH, and n is an integer of 0 to 20;

and wherein R$^2$ and R$^{2'}$ represent independently a hydrogen atom, a linear alkyl group, a branched alkyl group, a cycloalkyl group, an unsaturated hydrocarbon group, an aryl group, or a saturated or unsaturated hetero ring, and further provided that R$^1$ is not a hydrogen atom, a linear alkyl group or a branched alkyl group, wherein said film has a thickness of less that one micron.

2. The film for detecting chemical substances according to claim 1 wherein

X is H or CH$_3$;

R$^1$ is a substituted or unsubstituted aryl group or —Z—R$^2$;

Z is —O—, —(C=O)—O— or —O—(C=O)—;

and R$^2$ is a linear alkyl group, a branched alkyl group, a cycloalkyl group, an unsaturated hydrocarbon group, an aryl group, a saturated or unsaturated hetero ring or derivatives thereof.

3. The film for detecting chemical substances according to claim 1 wherein the polymer is crosslinked.

4. The film according to claim 1, wherein the film has a thickness of less than 50 nanometers.

5. The film according to claim 1, further provided that:

R$^1$ is not a hydrogen atom, a linear alkyl group or a branched alkyl group and in the case of a homopolymer is not an aryl group; and R$^2$ is not hydrogen.

6. The film according to claim 1, wherein the film comprises two or more polymers having different side chain groups.

7. The film according to claim 1, wherein the film comprises at least two films formed from different polymers.

8. The film according to claim 1, wherein the film comprises a random copolymer.

9. The film according to claim 1, wherein the film comprises an alternating copolymer.

10. The film according to claim 1, wherein the film comprises a block copolymer.

11. The film according to claim 1, wherein the film comprises a graft copolymer.

12. The film according to claim 1, wherein the film comprises at least one ester polymer selected from the group consisting of polymethhacrylic acid esters, polyacrylic acid esters and mixtures thereof.

13. The film according to claim 12, wherein said at least one ester polymer comprises side-chain groups selected from the group consisting of linear or branched alkyl groups, cycloalkyl groups or mixtures thereof.

14. A film according to claim 13, wherein said side-chain groups comprise from about 4 to about 22 carbon atoms.

15. The film according to claim 1, wherein the homopolymer or copolymer is cross-linked.

16. The film according to claim 1, wherein the homopolymer or copolymer further comprises cross-linking reactive groups.

17. The film according to claim 2, wherein the film comprises two or more polymers having different side chain groups.

* * * * *